US012697726B2

(12) United States Patent
Hu et al.

(10) Patent No.: US 12,697,726 B2
(45) Date of Patent: Aug. 4, 2026

(54) SAFETY AND CONTROL ENHANCEMENT IN TELE-OPERATED PHYSICAL HUMAN-ROBOT INTERACTIONS

(71) Applicant: Honda Motor Co., Ltd., Tokyo (JP)

(72) Inventors: Yuhan Hu, Santa Clara, CA (US); Rana Soltani Zarrin, Los Gatos, CA (US)

(73) Assignee: Honda Motor Co., Ltd., Tokyo (JP)

( * ) Notice: Subject to any disclaimer, the term of this patent is extended or adjusted under 35 U.S.C. 154(b) by 178 days.

(21) Appl. No.: 18/733,673

(22) Filed: Jun. 4, 2024

(65) Prior Publication Data

US 2025/0289142 A1     Sep. 18, 2025

Related U.S. Application Data

(60) Provisional application No. 63/564,897, filed on Mar. 13, 2024.

(51) Int. Cl.
   *B25J 9/16*          (2006.01)
   *A61B 34/00*        (2016.01)
   (Continued)

(52) U.S. Cl.
   CPC ............. *B25J 9/1674* (2013.01); *A61B 34/35* (2016.02); *A61B 34/74* (2016.02); *A61B 34/76* (2016.02); *B25J 13/081* (2013.01)

(58) Field of Classification Search
   CPC ....... B25J 9/1674; B25J 13/081; A61B 34/35; A61B 34/74; A61B 34/76
   (Continued)

(56) References Cited

U.S. PATENT DOCUMENTS 10,185,598 B2 *  1/2019  Wang .................... G06F 9/5088
11,197,799 B2 * 12/2021  Tian ....................... A61H 39/02
                (Continued)

OTHER PUBLICATIONS

Akalin et al, "Do you feel safe with your robot? Factors influencing perceived safety in human-robot interaction based on subjective and objective measures"; 2022, Elsevier. ScienceDirect Int Journal of Human-Computer Studies 158 (2022) 102744, pp. 1-16, https://doi.org/10.1016/j.ijhcs.2021.102744 (Year: 2022).*
(Continued)

*Primary Examiner* — Jaime Figueroa
(74) *Attorney, Agent, or Firm* — Suzanne Gagnon; American Honda Motor Co., Inc.

(57)          ABSTRACT

An electronic device and a method for safety and control enhancement in tele-operated physical human-robot interactions. The electronic device receives robot capability parameters, touch parameters, and control parameters to control physical interaction of the human machine interactions (HMI) device. The electronic device controls the physical interaction of the HMI device based on the robot capability parameters, the touch parameters, and the control parameters. The electronic device determines a physical response of the user, based on the control of the physical interaction of the HMI device and determines safety metrics of the user, based on the physical response, the robot capability parameters, and the touch parameters. The electronic device determines control metrics associated with an operator, based on the robot capability parameters, and the control parameters. The electronic device controls the physical interaction of the HMI device further based on the control metrics and the safety metrics.

20 Claims, 7 Drawing Sheets

(51) Int. Cl.
    *A61B 34/35*        (2016.01)
    *B25J 13/08*        (2006.01)
(58) Field of Classification Search
    USPC ................. 700/245–264; 318/568.11–568.25
    See application file for complete search history.

(56)                References Cited

U.S. PATENT DOCUMENTS

| | | | | |
|---|---|---|---|---|
| 11,472,028 | B2 * | 10/2022 | Laftchiev | B25J 9/1676 |
| 11,526,159 | B2 * | 12/2022 | Mcgregor | G06F 3/04815 |
| 12,271,582 | B2 * | 4/2025 | Zhao | G06F 3/0488 |
| 2011/0118752 | A1 * | 5/2011 | Itkowitz | B25J 9/1689 |
| | | | | 345/157 |
| 2011/0118753 | A1 * | 5/2011 | Itkowitz | A61B 34/74 |
| | | | | 606/130 |
| 2014/0100491 | A1 * | 4/2014 | Hu | A61H 3/008 |
| | | | | 601/23 |
| 2014/0150806 | A1 * | 6/2014 | Hu | B25J 11/009 |
| | | | | 901/1 |
| 2015/0314454 | A1 * | 11/2015 | Breazeal | G10L 15/32 |
| | | | | 700/259 |
| 2016/0151917 | A1 * | 6/2016 | Faridi | B25J 11/0015 |
| | | | | 700/259 |
| 2016/0193732 | A1 * | 7/2016 | Breazeal | B25J 11/0005 |
| | | | | 700/258 |
| 2016/0199977 | A1 * | 7/2016 | Breazeal | B25J 11/0015 |
| | | | | 700/246 |
| 2016/0238040 | A1 * | 8/2016 | Gallo | A61B 34/74 |
| 2016/0299796 | A1 * | 10/2016 | Wang | G05B 19/41835 |
| 2018/0081439 | A1 * | 3/2018 | Daniels | G06F 1/163 |
| 2018/0104542 | A1 * | 4/2018 | Kwon | A63B 21/4015 |
| 2018/0250086 | A1 * | 9/2018 | Grubbs | A61B 34/35 |
| 2020/0121556 | A1 * | 4/2020 | Tian | A61H 39/02 |
| 2021/0085558 | A1 * | 3/2021 | Shin | A61H 9/0078 |
| 2021/0170590 | A1 * | 6/2021 | Laftchiev | B25J 9/163 |
| 2021/0255611 | A1 * | 8/2021 | McGregor | G06T 13/20 |
| 2022/0354597 | A1 * | 11/2022 | Kaouk | A61B 34/30 |
| 2023/0064632 | A1 * | 3/2023 | Mcgregor | G06F 3/011 |
| 2023/0347210 | A1 * | 11/2023 | McInturf | G06T 13/80 |
| 2023/0414430 | A1 * | 12/2023 | Godlasky | A61G 13/08 |
| 2024/0025034 | A1 * | 1/2024 | Lachenmayr | B25J 3/00 |
| 2024/0086049 | A1 * | 3/2024 | Zhao | G06F 40/134 |
| 2024/0122783 | A1 * | 4/2024 | Blankenship | A61H 23/02 |

OTHER PUBLICATIONS

Airosa, et al., "Tactile massage as part of the caring act: A qualitative study in short-term emergency wards", Qualitative Research, Journal of Holistic Nursing, Sep. 16, 2015, 11 pages.

Cocksedge, et al., "Touch in primary care consultations: qualitative investigation of doctors' and patients' perceptions", British Journal of General Practice, Apr. 2013, 08 pages.

Connor, et al., "Intentional comfort touch a conceptual model", Journal of Holistic Nursing, 2009, pp. 127-135.

Figma, 2023, URL: https://www.figma.com/.

Haddadin, et al., "Requirements for safe robots: Measurements, analysis and new insights", The International Journal of Robotics Research, Aug. 20, 2009, 21 pages.

Haddadin, et al., "The Franka Emika Robot: A Reference Platform for Robotics Research and Education", IEEE Robotics & Automation Magazine, vol. 29, Issue: 2, Jun. 2022, pp. 46-64.

Hamad, et al., "A Concise Overview of Safety Aspects in Human-Robot Interaction", arXiv, Safety Aspects in Human-Robot Interaction, Sep. 18, 2023, 15 pages.

Hollinger, et al., "Factors influencing the perception of touch by elderly nursing home residents and their health caregivers", International Journal of Nursing Studies, vol. 30, Issue 5, Oct. 1993, pp. 445-461.

Law, et al., "A touching connection: how observing robotic touch can affect human trust in a robot", International Journal of Social Robotics, Jan. 5, 2021, 17 pages.

O'Lynn, et al., "How Should I Touch You?: A Qualitative Study of Attitudes on Intimate Touch in Nursing Care", The American Journal of Nursing, 2011, 9 pages.

Pedrazza, et al., "Variables of Individual Difference and the Experience of Touch in Nursing", Western Journal of Nursing Research, 2018, pp. 1614-1637.

Pedrazza, et al., "Development and Initial Validation of the Nurses' Comfort With Touch Scale", Springer Publishing Company, 2015, pp. 364-378.

Qbrobotics, qb SoftHand2 Research, 2023, URL: https://qbrobotics.com/product/qb-softhand-2-research/.

Pirkko Routasalo, "Physical touch in nursing studies: a literature review", Journal of Advanced Nursing, Dec. 25, 2001.

Thompson, et al., "Social factors in human-robot interaction", In Human-robot interactions in future military operations CRC Press, 2016, pp. 67-82.

Erp, et al., "How to touch humans: Guidelines for social agents and robots that can touch", In 2013 humaine association 4conference on affective computing and intelligent interaction, IEEE, 2013, pp. 780-785.

Willemse, et al., "Social Touch in Human-Robot Interaction: Robot-Initiated Touches can Induce Positive Responses without Extensive Prior Bonding", International Journal of Social Robotics, Nov. 8, 2018, pp. 285-304.

Yohanan, et al., "The role of affective touch in human-robot interaction: Human intent and expectations in touching the haptic creature", International Journal of Social Robotics, 2012, pp. 163-180.

\* cited by examiner

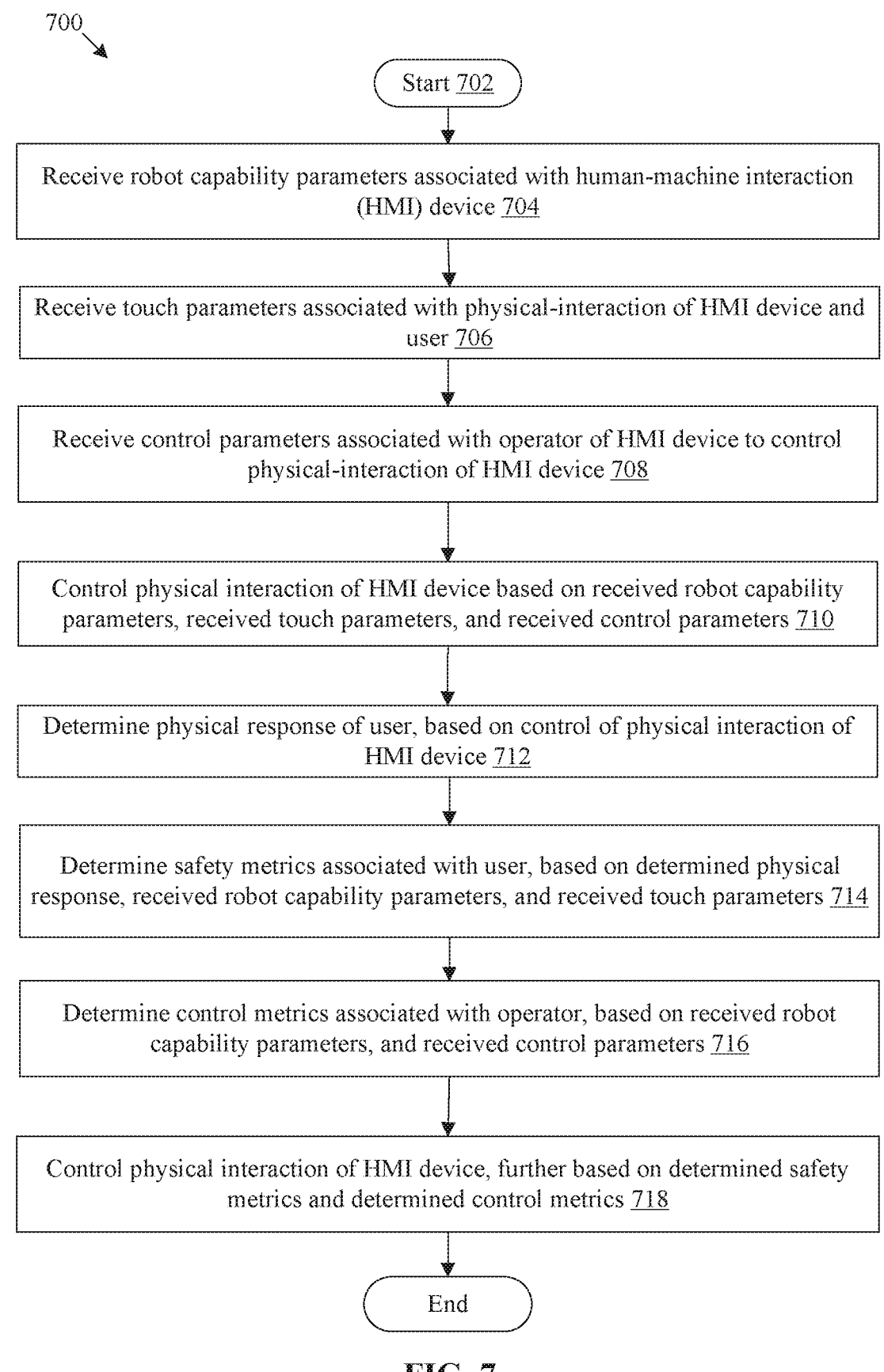

Start 702

Receive robot capability parameters associated with human-machine interaction (HMI) device 704

Receive touch parameters associated with physical-interaction of HMI device and user 706

Receive control parameters associated with operator of HMI device to control physical-interaction of HMI device 708

Control physical interaction of HMI device based on received robot capability parameters, received touch parameters, and received control parameters 710

Determine physical response of user, based on control of physical interaction of HMI device 712

Determine safety metrics associated with user, based on determined physical response, received robot capability parameters, and received touch parameters 714

Determine control metrics associated with operator, based on received robot capability parameters, and received control parameters 716

Control physical interaction of HMI device, further based on determined safety metrics and determined control metrics 718

End

FIG. 7

SAFETY AND CONTROL ENHANCEMENT IN TELE-OPERATED PHYSICAL HUMAN-ROBOT INTERACTIONS

CROSS-REFERENCE TO RELATED APPLICATIONS/INCORPORATION BY REFERENCE

This Application also makes reference to U.S. Provisional Application Ser. No. 63/564,897, which was filed on Mar. 13, 2024. The above stated Patent Application is hereby incorporated herein by reference in its entirety.

BACKGROUND

Advancements in the field of engineering and technology have led to the development and proliferation of various human-machine interaction (HMI) devices, such as robots. Recently, robots are increasingly being used to perform or assist in many complex and risky tasks, such as for remote robotic surgeries. The importance of safety and control measures in robotics cannot be overstated, as they are crucial for safeguarding humans from the inherent dangers of robotic activities. Safe robotic operation is achieved by reducing human involvement in dangerous tasks, averting injuries due to repetitive motions or strenuous lifting, and addressing risks linked to worker fatigue. Nonetheless, the adoption of robots can introduce new challenges, such as ergonomic concerns, possible errors in control systems, and the imperative need for thorough training. In essence, robotic safety is a comprehensive concept that includes physical safety, digital security, and psychological health, all of which demand the continuous focus of regulatory bodies and industry authorities to uphold stringent safety protocols. Existing robotic systems often overlook the nuances of physical human-robot interaction (pHRI), particularly in the context of teleoperated robots used in healthcare settings. Additionally, these systems do not adequately reflect the experiences of both the operator and the recipient, which are facilitated through the robot's mediation.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

According to an embodiment of the disclosure, an electronic device for safety and control enhancement in tele-operated physical human-robot interactions is provided. The electronic device may include circuitry that may be configured to receive robot capability parameters associated with a human machine interaction (HMI) device and receive touch parameters associated with a physical interaction of the HMI device and a user. Further the circuitry may be configured to receive control parameters associated with an operator of the HMI device to control the physical interaction of the HMI device based on the received robot capability parameters, the received touch parameters, and the received control parameters. Further the circuitry may be configured to determine a physical response of the user, based on the control of the physical interaction of the HMI device and further determine safety metrics associated with the user, based on the determined physical response, the received robot capability parameters, and the received touch parameters. Also, the circuitry may be configured to determine control metrics associated with the operator, based on the received robot capability parameters, and the received control parameters and control the physical interaction of the HMI device, further based on the determined safety metrics and the determined control metrics.

According to another embodiment of the disclosure, a method for safety and control enhancement in tele-operated physical human-robot interactions is provided. The method may include receive robot capability parameters associated with a human machine interaction (HMI) device and receive touch parameters associated with a physical interaction of the HMI device and a user. Further the method may include receiving control parameters associated with an operator of the HMI device to control the physical interaction of the HMI device based on the received robot capability parameters, the received touch parameters, and the received control parameters. Further the method may include determining a physical response of the user, based on the control of the physical interaction of the HMI device and further determining safety metrics associated with the user, based on the determined physical response, the received robot capability parameters, and the received touch parameters. Also, the method may include determining control metrics associated with the operator, based on the received robot capability parameters, and the received control parameters and controlling the physical interaction of the HMI device, further based on the determined safety metrics and the determined control metrics.

According to another embodiment of the disclosure, a non-transitory computer-readable medium is provided. The non-transitory computer-readable medium may have stored thereon computer implemented instructions that, when executed by an electronic device, causes the electronic device to execute operations. The operations may include receiving robot capability parameters associated with a human-machine interaction (HMI) device and receiving touch parameters associated with a physical-interaction of the HMI device and a user. The operations may further include reception control parameters associated with an operator of the HMI device to control the physical interaction of the HMI device. The operations may further include control of the physical interaction of the HMI device based on the received robot capability parameters, the received touch parameters, and the received control parameters. The operations may further include determination of a physical response of the user, based on the control of the physical interaction of the HMI device and determination of safety metrics associated with the user, based on the determined physical response, the received robot capability parameters, and the received touch parameters. Also, the operations may further include determination of control metrics associated with the operator, based on the received robot capability parameters, and the received control parameters and further controlling the physical interaction of the HMI device, further based on the determined safety metrics and the determined control metrics.

BRIEF DESCRIPTION OF THE DRAWINGS

FIG. 6 is a diagram that illustrates an exemplary scenario of a tele-operated human-robot interaction to control physical interaction of the HMI device, in accordance with an embodiment of the disclosure.

FIG. 7 is a flowchart that illustrates operations of an exemplary method for safety and control enhancement in tele-operated physical huma-robot interactions, in accordance with an embodiment of the disclosure.

DETAILED DESCRIPTION

Figure 1:
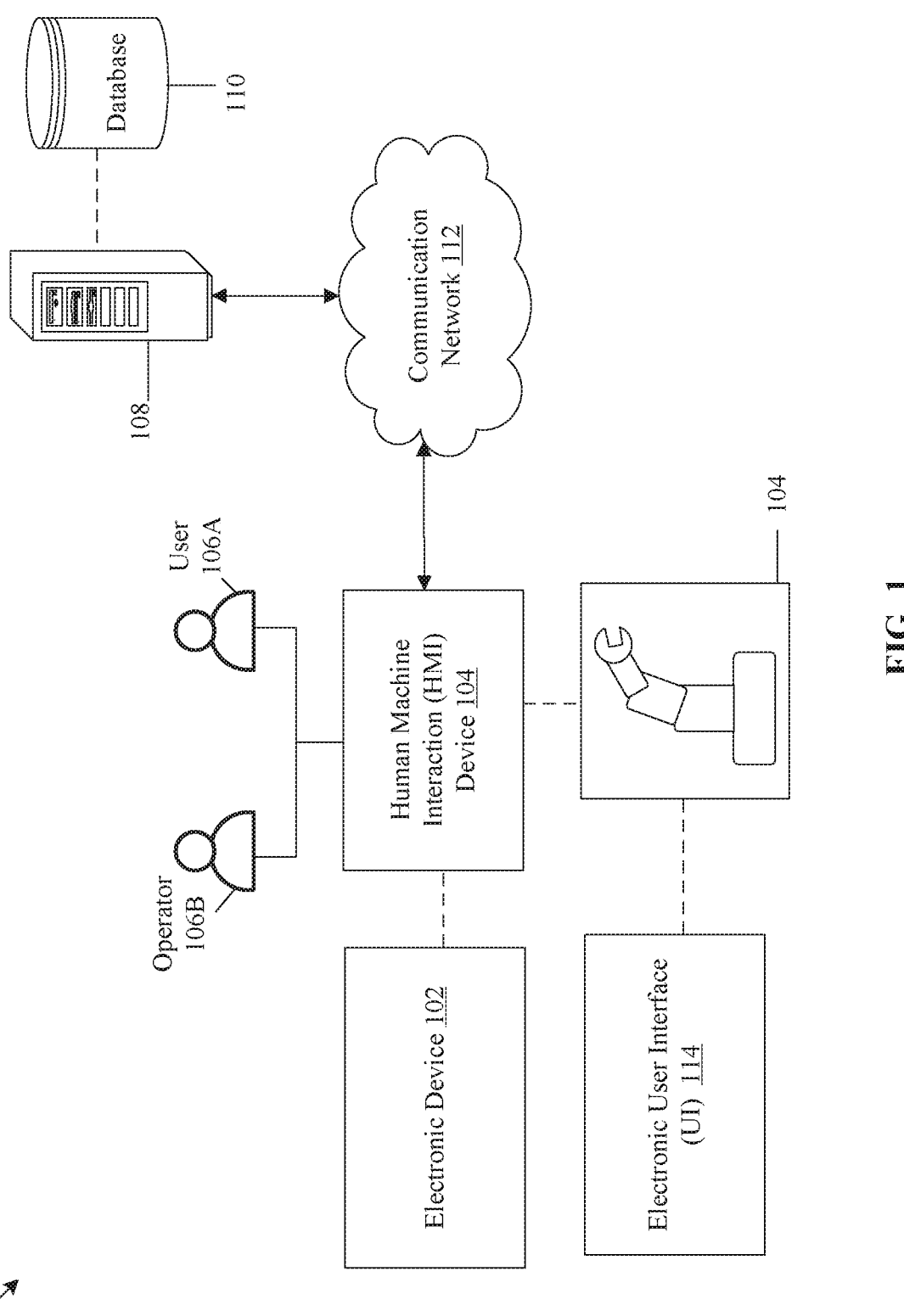
FIG. 1 is a diagram that illustrates an exemplary network environment for safety and control enhancement in tele-operated physical human-robot interaction (pHRI), in accordance with an embodiment of the disclosure.

The following described implementation may be found in an electronic device and method for safety and control enhancement in tele-operated physical human-robot interactions (pHRI). Exemplary aspects of the disclosure may provide an electronic device (for example, a mobile phone, a smart phone, a desktop, a laptop, a personal computer, and the like) that may receive robot capability parameters (e.g., form factor parameters, level of autonomy, degree of freedom) associated with a human-machine interaction device (e.g., robots). Next, the electronic device may receive touch parameters (e.g., orientation, speed, force, time, contact zone, etc.) associated with a physical-interaction of the HMI device and a user (e.g., a patient) and receive control parameters (e.g., operator-control freedom parameters, touch-based feedback, user interface control, etc.) associated with an operator of the HMI device to control the physical-interaction of the HMI device. Further, the electronic device may control the physical interaction of the HMI device based on the received robot capability parameters, the received touch parameters, and the received control parameters to determine a physical response of the user, based on the control of the physical interaction of the HMI device. Furthermore, the electronic device may determine a physical response of the user, based on the control of the physical interaction of the HMI device and determine safety metrics associated with the user, based on the determined physical response, the received robot capability parameters, and the received touch parameters. Furthermore, the electronic device may determine control metrics associated with the operator, based on the received robot capability parameters, and the received control parameters and control the physical interaction of the HMI device, further based on the determined safety metrics and the determined control metrics.

Typically, most existing HMI devices may be focused on tele-operated human-human interaction methods for determination and control of the tele-operated human robot interaction. While there are several exploratory methods available, they primarily rely on physical interaction of the HMI device. However, in the context of pHRI, the end-user experience may be difficult to fully recreate through a tele-medium. In order to address such issues, the disclosed electronic device may receive robot capability parameters associated with a HMI device and also receive touch parameters associated with a physical interaction of the HMI device and the user. The electronic device may receive control parameters associated with an operator of the HMI device to control the physical interaction of the HMI device. The electronic device may further control the physical interaction of the HMI device based on the received robot capability parameters, the received touch parameters, and the received control parameters and determine a physical response of the user, based on the control of the physical interaction of the HMI device. The electronic device may determine safety metrics associated with the user, based on the determined physical response, the received robot capability parameters, and the received touch parameters and determine control metrics associated with the operator, based on the received robot capability parameters, and the received control parameters. Finally, the electronic device may control the physical interaction of the HMI device, based on the determined safety metrics and the determined control metrics.

The electronic device of the disclosure may enable a human-robot interaction to gather insights and ground robot design choices when investigating physical human-robot interaction scenarios, especially in the tele-operated health care that involves instrumental touch interactions. In essence, the outcomes of HRI may be pivotal for those creating future tele-operated healthcare robots. It emphasizes the importance of understanding the nuances of physical interactions between humans and robots to design systems that are effective, safe, and user-friendly. This is particularly relevant in healthcare settings where precision and reliability are critical. For example, based on the physical response of the user safety metrics of the user may be determined. Also, the physical interaction of the HMI device may be controlled based on the safety metrics and the determined control metrics. The method may include a two-step co-design experimental procedure, a user interface that helps users select robot settings, and evaluation tools that measure the interaction experience of the user with the robot using both numbers and words, with an emphasis on safety and comfort. Therefore, both qualitative measures and quantitative measures may be used to enhance user experience of the HMI devices, focusing on safety and comfort. This may further enhance safety and control of the HMI device in performing the relevant action involving an end-user.

FIG. 1 is a diagram that illustrates an exemplary network environment for safety and control enhancement in tele-operated physical HMI device, in accordance with an embodiment of the disclosure. With reference to FIG. 1, there is shown a network environment 100. The network environment 100 includes an electronic device 102, a human machine interaction (HMI) device 104, a server 108, a database 110, and a communication network 112. The electronic device 102, the HMI device 104, and the server 108 may communicate with one another through one or more networks (such as the communication network 112). The server 108 may be associated with the database 110. FIG. 1 also shows an electronic user interface (UI) 114 associated with or hosted on the HMI device 104. Though not shown, but in certain cases, the electronic UI 114 may be associated with or hosted on the electronic device 102. In FIG. 1, there is also shown, a user 106A and an operator 106B associated with (or who may operate) the electronic device 102 and/or the HMI device 104. Though only one user (i.e., the user 106A) and only one operator (i.e., the operator 106B) is shown, the scope of the disclosure may not be so limited. In some embodiments, the operator 106B may be, for example, a remote operator, a surgeon, and the like, may be associated with the electronic device 102. Further, the user 106A may be (different from the operator 106B), for example, an end-user, such as a patient, may be associated with (or may interact with) the HMI device 104.

The electronic device 102 may include suitable logic, circuitry, interfaces, and/or code that may be configured to receive robot capability parameters (e.g., form factor parameter, level of autonomy, degree of freedom), touch parameters (e.g., orientation, speed, force, time duration, and contact zone) and control parameters (e.g., operator-control freedom parameters, touch-based-feedback, user interface control). The electronic device 102 may control the physical interaction of the HMI device (e.g., the HMI device 104) based on the received robot capability parameters, the received touch parameters, and the received control parameters. The electronic device 102 may determine a physical response of the user 106A, based on the control of the physical interaction of the HMI device (e.g., the HMI device 104). The physical response of the user 106A may include, but is not limited to, a body movement of the user 106A, a gaze of the user 106A, a verbal response of the user 106A, and a facial response of the user 106A. The electronic device 102 may determine safety metrics associated with the user 106A, based on the determined physical response, the received robot capability parameters, and the received touch parameters. The safety metrics may include, but is not limited to, a trust level of the user associated with the HMI device 104, a comfort level of the user 106A associated with the HMI device 104, and a safety level of the user 106A associated with the HMI device 104. Further, the electronic device 102 may determine the control metrics associated with the operator 106B, based on the received robot capability parameters, and the received control parameters. The control metrics may include, but is not limited to, a physical load on the operator 106B, a mental load on the operator 106B, a level of control of the operator 106B, a level of awareness of the operator 106B, and a task performance by the HMI device 104. Also, the electronic device 102 may receive user-background parameters and operator-background parameters associated with the HMI device 104. The electronic device 102 may control the physical interaction of the HMI device 104, based on the determined safety metrics and the determined control metrics. The electronic device 102 may transmit instructions to the HMI device 104 to control the rendering of the electronic UI 114, in case the electronic UI 114 is hosted on the HMI device 104. In case, the electronic UI 114 is hosted on the electronic device 102, the electronic device 102 may control the rendering of the electronic UI 114 on the electronic device 102. Examples of the electronic device 102 may include, but are not limited to, a desktop, a tablet, a television (TV), a laptop, a computing device, a smartphone, a cellular phone, a mobile phone, a consumer electronic (CE) device having a display.

The HMI device 104 may include suitable logic, circuitry, interfaces, and/or code that may be configured to perform a predetermined set of actions that may involve a physical interaction of the HMI device 104 and the user 106A. The operations of the HMI device 104 may be controlled based on the robot capability parameters, the touch parameters, and the control parameters. In an example, the HMI device 104 may host the electronic UI 114. The electronic UI 114 may enable reception of the robot capability parameters, the touch parameters, and the control parameters. Based on the reception of the various parameters, the physical interactions of the HMI device 104 may be controlled. The operations (e.g., the physical interactions) of the HMI device 104 may be accordingly controlled based on the determined safety metrics and the determined control metrics. Examples of the HMI device 104 may include, but are not limited to, a robotic arm, a humanoid, a human-interfaced machine, an industrial machine, or any device including software and hardware for touch-based human-machine interaction.

The server 108 that may include suitable logic, circuitry, interfaces, and/or code configured to receive requests from the electronic device 102 to receive parameters from the user 106A. The server 108 may be configured to extract input parameters (e.g., robot capability parameters, touch parameters, and control parameters) associated with the physical interaction of the HMI device 104 and the user 106A. Further, the server 108 may be configured to extract user input for the extracted parameters (e.g., robot capability parameters, touch parameters, and control parameters) based on the control of the rendering of an electronic UI (e.g., the electronic UI 114) on the HMI device 104. The server 108 may be configured to extract control metrics and safety metrics determined based on the physical response of the user 106A. The server 108 may also extract user-background parameters associated with the user 106A, and the operator background parameters associated with the operator 106B. The user-background parameters may include a physical condition of the user 106A, an age of the user 106A, a gender of the user 106A, an ethnicity of the user 106A and so on. The operator background parameters may include an identity of the operator 106B, a type of operation of the operator 106B, a gender of the operator 106B, a relationship between a patient (e.g., the user 106A) and the operator 106B, and so on.

The server 108 may execute operations through web applications, cloud applications, HTTP requests, repository operations, file transfer, and the like. Example implementations of the servers 108 may include, but are not limited to, a database server, a file server, a web server, an application server, a mainframe server, a cloud computing server, or a combination thereof. In at least one embodiment, the server 108 may be implemented as a plurality of distributed cloud-based resources by use of several technologies that are well known to those ordinarily skilled in the art. A person with ordinary skill in the art will understand that the scope of the disclosure may not be limited to the implementation of the server 108 and the electronic device 102 as separate entities.

The database 110 may include suitable logic, circuitry, interfaces, and/or code configured to store information, such as various parameters (robot capability parameters, touch parameters, control parameters) received from the user (e.g., the user 106A) or the operator 106B. Further, the database 110 may store information associated with instructions associated with an operation of the HMI device 104. For example, the database 110 may store a mapping table including predefined instructions associated with different values of the parameters to control the operations of the HMI device 104. The database 110 may be derived from data of a relational or non-relational database or a set of comma-separated values (csv) files in conventional or big-data storage. The database 110 may be stored or cached on device or server, such as the server 108. The device storing the database 110 may be configured to query the database 110 for certain information (such as the information related to a user input associated with the various parameters, and the information related to the mapping table) based on reception of a request for the particular information from the electronic device 102. In response, the device storing the database 110 may be configured to retrieve, from the database 110, results (for example, the user input associated with the various parameters, a user-feedback associated with the touch-interaction, and/or the mapping table) based on the received query.

In some embodiments, the database 110 may be hosted on a server 108 located at same or different locations. The operations of the database 110 may be implemented using hardware including a processor, a microprocessor (e.g., to perform or control performance of one or more operations), a field-programmable gate array (FPGA), or an application-specific integrated circuit (ASIC). In some other instances, the database 110 may be implemented using software.

The communication network 112 may include a communication medium through which the electronic device 102, HMI device 104, and the server 108 may communicate with each other. The communication network 112 may be a wired or wireless communication network 112. Examples of the communication network 112 may include, but are not limited to, Internet, a cloud network, Cellular or Wireless Mobile Network (such as Long-Term Evolution and 5ᵗʰ Generation (5G) New Radio (NR)), satellite communication system (using, for example, low earth orbit satellites), a Wireless Fidelity (Wi-Fi) network, a Personal Area Network (PAN), a Local Area Network (LAN), or a Metropolitan Area Network (MAN). Various devices in the network environment 100 may be configured to connect to the communication network 112, in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols.

In operation, the electronic device 102 may be configured to enhance the safety and control in tele-operated physical human-robot interactions based on user input of various parameters, such as robot capability parameters, touch parameters, and control parameters associated with the HMI device 104 and the user 106A. In an embodiment, the electronic device 102 may be configured to receive the robot capability parameters associated with the HMI device 104. In an example, the robot capability parameters associated with a physical interaction of the HMI device 104 may include a form factor parameter of the HMI device 104, a level of autonomy of the HMI device 104, a degree of freedom of the HMI device 104, etc. The reception of the robot capability parameters is described further, for example, in FIG. 4 (at 402).

In an embodiment, the electronic device 102 may be configured to receive the touch parameters associated with a physical interaction of the HMI device 104 and a user (e.g., the user 106A). The touch parameters may include an orientation, a speed, a force, a time duration, a contact zone, and so on, of the HMI device 104 with respect to the user 106A. The reception of the touch parameters is described further, for example, in FIG. 4 (at 404).

The electronic device 102 may be configured to receive the control parameters associated with an operator (e.g., the operator 106B) of the HMI device 104 to control the physical interaction of the HMI device 104. The control parameters may include an operator-control freedom parameters, a touch-based feedback, a user interface control, and the like. The reception of the control parameters is described further, for example, in FIG. 4 (at 406).

The electronic device 102 may be configured to control the physical interaction of the HMI device (e.g., the HMI device 104) based on the received robot capability parameters, the received touch parameters, and the received control parameters. For example, the electronic device 102 may determine set of instructions associated with the physical interaction, based on the received robot capability parameters, the received touch parameters, and the received control parameters. Thereafter, the electronic device 102 may transmit the determined set of instructions to the HMI device 104 to control an operation of the HMI device 104 and thereby control the physical interaction of the HMI device 104 with the user 106A. The control of the physical interaction is described further, for example, in FIG. 4 (at 408).

The electronic device 102 may be configured to determine the physical response of the user 106A, based on the control of the physical interaction of the HMI device (e.g., the HMI device 104). The physical response of the user 106A may include, but is not limited to, a body movement of the user 106A, a gaze of the user 106A, a verbal response of the user 106A, and a facial response of the user 106A. The determination of the physical response of the user is described further, for example, in FIG. 4 (at 410).

The electronic device 102 may be configured to determine the safety metrics associated with the user 106A, based on the determined physical response, the received robot capability parameters, and the received touch parameters. The safety metrics may include, but is not limited to, a trust level of the user associated with the HMI device 104, a comfort level of the user 106A associated with the HMI device 104, and a safety level of the user 106A associated with the HMI device 104. The determination of the safety metrics is described further, for example, in FIG. 4 (at 412).

The electronic device 102 may determine the control metrics associated with the operator 106B, based on the received robot capability parameters, and the received control parameters. The control metrics may include, but is not limited to, a physical load on the operator 106B, a mental load on the operator 106B, a level of control of the operator 106B, a level of awareness of the operator 106B, and a task performance by the HMI device 104. The determination of the control metrics is described further, for example, in FIG. 4 (at 414).

In an embodiment, the electronic device 102 may receive the user-background parameters associated with the user 106A. The received user-background parameters may include a physical condition (for example, accessibility, tactile feedback, environmental adaption, etc.) of the user 106A, an age (ranging, for example, from 0 to 100 years), a gender (for example, male or female), and an ethnicity (for example, cultural norms) of the user 106A. The received user-background parameters may be correlated with the trust level of the user 106A associated with the HMI device 104.

In an embodiment, the electronic device 102 may receive the operator-background parameters associated with the operator 106B. The received operator-background parameters may include an identity of the operator 106B (for example, a remote operator, a surgeon, and the like), a type of operation of the operator 106B (for example, monitoring, control, data entry, and the like), a gender of the operator 106B (for example, male or female), and a relationship between a patient/user 106A and the operator 106B. The received operator-background parameters may be correlated with the trust level of the user 106A associated with the HMI device 104.

The electronic device 102 may control the physical interaction of the HMI device 104, based on the determined safety metrics and the determined control metrics. The electronic device 102 may transmit instructions to the HMI device 104 to control the physical interaction and also control the rendering of the electronic UI 114. The control of the physical interaction of the HMI device is described further, for example, in FIG. 4 (at 416).

Figure 2:
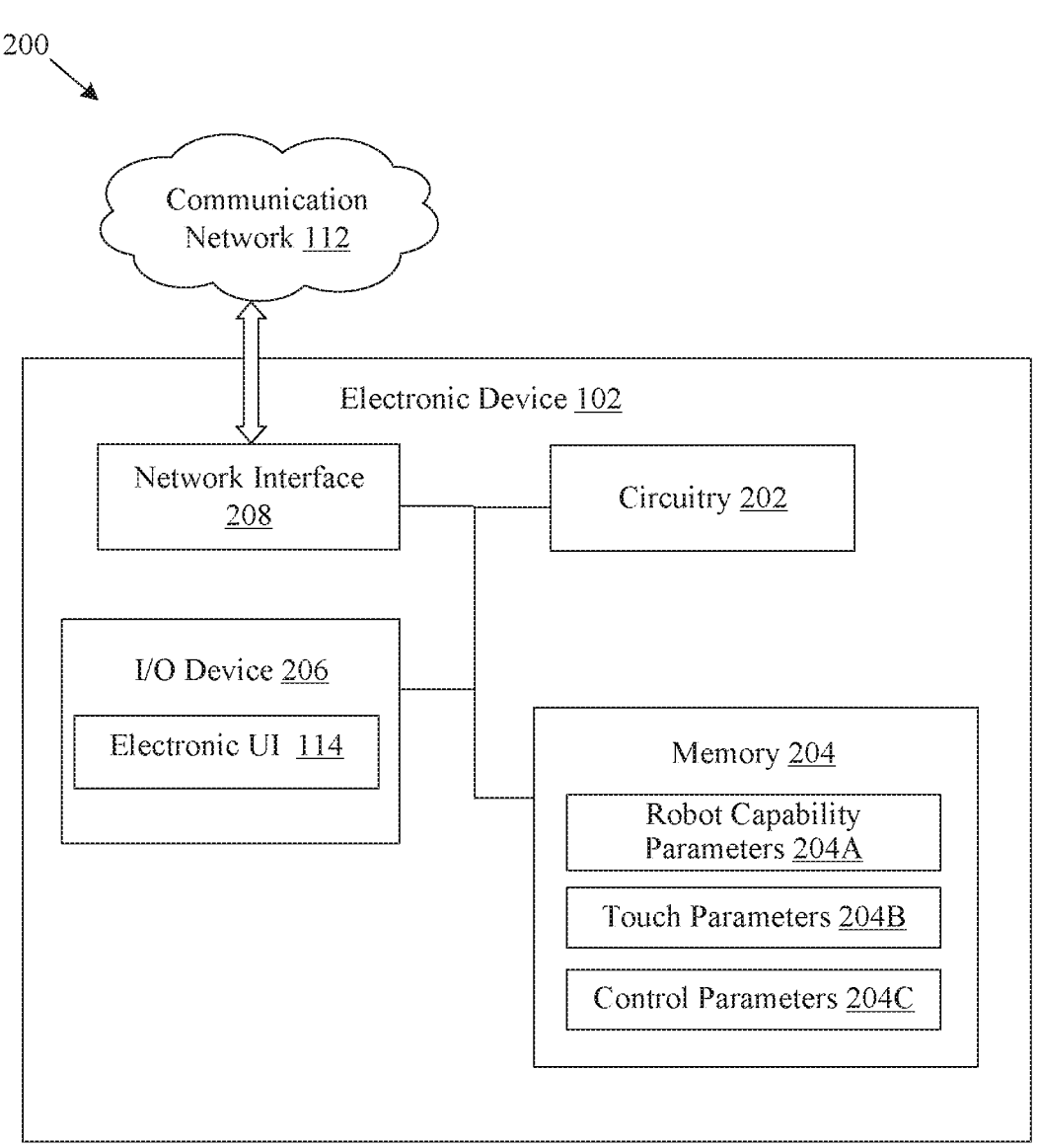
FIG. 2 is a block diagram that illustrates an exemplary electronic device of FIG. 1, in accordance with an embodiment of the disclosure.

FIG. 2 is a block diagram that illustrates an exemplary electronic device of FIG. 1, in accordance with an embodiment of the disclosure. FIG. 2 is explained in conjunction with elements from FIG. 1. With reference to FIG. 2, there is shown a block diagram 200 of the electronic device 102. The electronic device 102 may include a circuitry 202, a memory 204, an input/output (I/O) device 206, and a network interface 208. In at least one embodiment, the I/O device 206 may also include the electronic UI 114. In at least one embodiment, the memory 204 may include parameters (for example, robot capability parameters 204A, touch parameters 204B, control parameters 204C, and safety metrics). The circuitry 202 may be communicatively coupled to the memory 204, the I/O device 206, the network interface 208, through wired or wireless communication of the electronic device 102.

The circuitry 202 may include suitable logic, circuitry, and interfaces that may be configured to execute program instructions associated with different operations to be executed by the electronic device 102. The operations may include controlling the physical interaction of the HMI device 104 based on the received robot capability parameters 204A, the received touch parameters 204B, and the received control parameters 204C. The operations may further include determination of the physical response of the user 106A and determination of the safety metrics, and the control metrics based on the robot capability parameters 204A and control parameters 204C.

The circuitry 202 may include one or more specialized processing units, which may be implemented as an integrated processor or a cluster of processors that perform the functions of the one or more specialized processing units, collectively. The circuitry 202 may be implemented based on a number of processor technologies known in the art. Examples of implementations of the circuitry 202 may be an x86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other computing circuits.

The memory 204 may include suitable logic, circuitry, interfaces, and/or code that may be configured to store the program instructions to be executed by the circuitry 202. The program instructions stored on the memory 204 may enable the circuitry 202 to execute operations of the circuitry 202 (and/or the electronic device 102). In at least one embodiment, the memory 204 may store the parameters (for example, the robot capability parameters 204A, the touch parameters 204B, the control parameters 204C, and the safety metrics). The robot capability parameters 204A associated with the HMI device 104 may include the form factor parameter, the level of autonomy, and the degree of freedom and so on. The touch parameters 204B may include the orientation, speed, force, time duration, contact zone and so on. The control parameters 204C may include the operator-control freedom parameters, the touch-based feedback, the user interface control and the like. The determined safety metrics may include the trust level of the user 106A, comfort level of the user 106A, safety level of the user 106A and the like. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 206 may include suitable logic, circuitry, interfaces, and/or code that may be configured to receive an input and provide an output based on the received input. For example, the I/O device 206 may receive a user input from the user 106A or the operator 106B. The reception of various parameters (e.g., the robot capability parameters 204A, the control parameters 204C, and the like) may be indicative of operating parameters for the HMI device 104. In some embodiments, the I/O device 206 may receive the robot capability parameters 204A, the touch parameters 204B, and the control parameters 204C.

The input of the parameters may be received from the user 106A for controlling the HMI device 104 to operate based on the various parameters. Examples of the I/O device 206 may include, but are not limited to, a touch screen, a keyboard, a mouse, a joystick, a microphone, a display device, and a speaker. Examples of the I/O device 206 may further include braille I/O devices, such as braille keyboards and braille readers.

The I/O device 206 may include the electronic UI 114. The electronic UI 114 may include suitable logic, circuitry, and interfaces that may be configured to receive inputs from the circuitry 202 to render, on a display screen, for example, the robot capability parameters 204A, touch parameters 204B, control parameters 204C, and the like. In an embodiment, the electronic UI 114 may correspond to a display device associated with the electronic device 102. In at least one embodiment, the electronic UI 114 may be at least one of a resistive touch screen, a capacitive touch screen, or a thermal touch screen. The electronic UI 114 may be realized through several known technologies such as, but not limited to, at least one of a Liquid Crystal Display (LCD) display, a Light Emitting Diode (LED) display, a plasma display, or an Organic LED (OLED) display technology, or other display devices.

The network interface 208 may include suitable logic, circuitry, and interfaces that may be configured to facilitate communication between the electronic device 102, the HMI device 104, and the server 108, via the communication network 112. The network interface 208 may be implemented by use of various known technologies to support wired or wireless communication of the electronic device 102 with the communication network 112. The network interface 208 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry.

The network interface 208 may be configured to communicate via wireless communication with networks, such as the Internet, an Intranet, or a wireless network, such as a cellular telephone network, a wireless local area network (LAN), a short-range communication network 112, and a metropolitan area network (MAN). The wireless communication may use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), $5^{th}$ Generation (5G) New Radio (NR), code division multiple access (CDMA), time division multiple access (TDMA), Bluetooth, Wireless Fidelity (Wi-Fi) (such as IEEE 802.11a, IEEE 802.11b, IEEE 802.11g or IEEE 802.11n), voice over Internet Protocol (VoIP), light fidelity (Li-Fi), Worldwide Interoperability for Microwave Access (Wi-MAX), a near field communication protocol, and a wireless pear-to-pear protocol.

Figure 3:
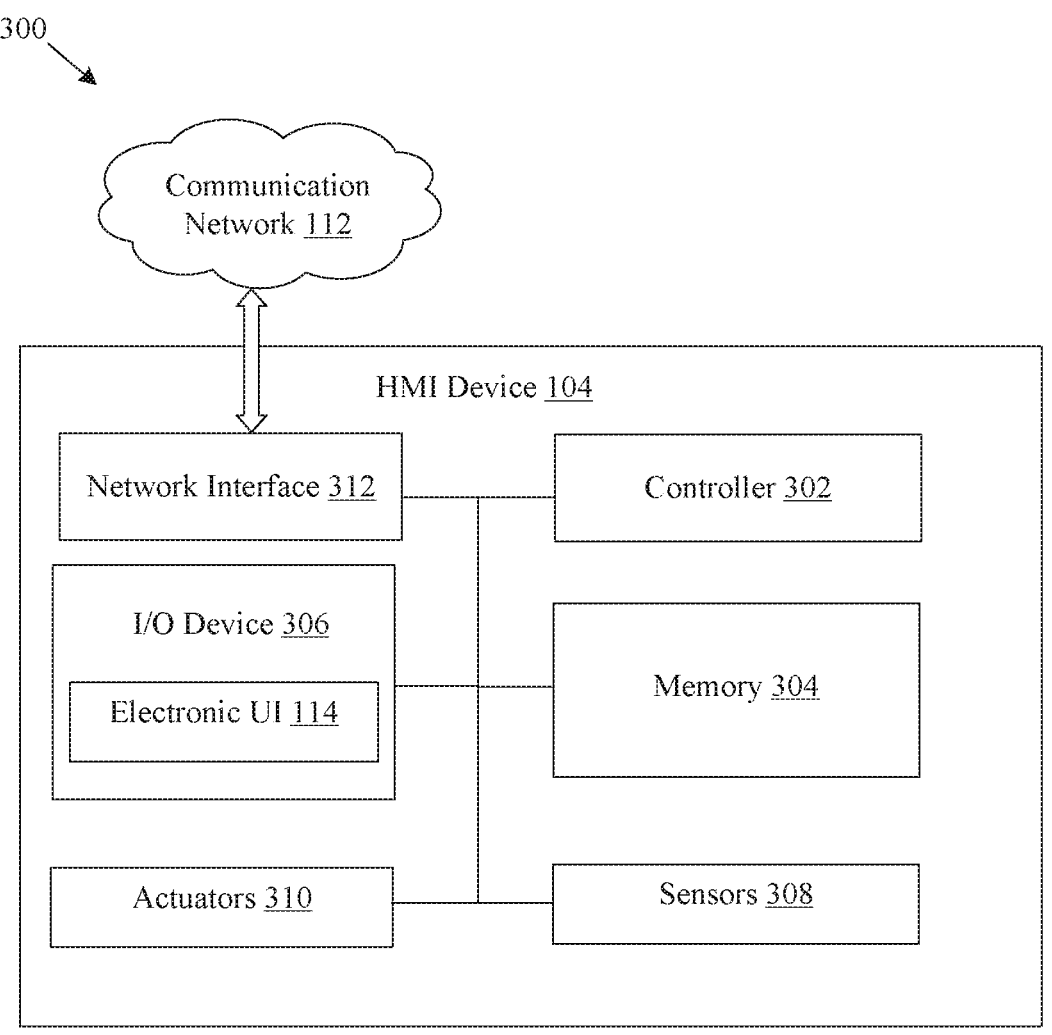
FIG. 3 is a block diagram that illustrates an exemplary HMI device of FIG. 1, in accordance with an embodiment of the disclosure.

FIG. 3 is a block diagram that illustrates an exemplary HMI device of FIG. 1, in accordance with an embodiment of the disclosure. FIG. 3 is explained in conjunction with elements from FIG. 1 and FIG. 2. With reference to FIG. 3, there is shown a block diagram 300 of the HMI device 104. The HMI device 104 may include a controller 302, a memory 304, an input/output (I/O) device 306, sensors 308, actuators 310, and a network interface 312. In at least one embodiment, the I/O device 306 may also include the electronic UI 114. The controller 302 may be communicatively coupled to the memory 304, the I/O device 306, the network interface 312, the sensors 308, and actuators 310 through wired or wireless communication of the HMI device 104.

The controller 302 may include suitable logic, circuitry, and interfaces that may be configured to execute program instructions associated with different operations to be executed by the HMI device 104. The controller 302 may be a computer system that connects to the HMI device 104 in order to control the physical interaction. The controller 302 may transmit control commands to the various components of the HMI device 104 to control the physical interaction. In addition to physical interaction, the controller 302 may also be responsible for end-effector and to prevent interference from occurring within the environment. Robotic programs may be coded into the controller 302, which may be the electronic device 102 that may include buttons, switches, or a touchscreen to allow for the input of programming commands of the robotic programs.

The memory 304 may include suitable logic, circuitry, interfaces, and/or code that may be configured to store the program instructions to be executed by the controller 302. The program instructions stored on the memory 304 may enable the controller 302 to execute operations of the controller 302 (and/or the HMI device 104). In at least one embodiment, the memory 304 may store the parameters. The parameters may include, but are not limited to, the robot capability parameters 204A, the touch parameters 204B, and the control parameters 204C. Examples of implementation of the memory 304 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 306 may include suitable logic, circuitry, interfaces, and/or code that may be configured to receive an input and provide an output based on the received input. For example, the I/O device 306 may receive a user input from the user 106A. The user input may be indicative of parameters (for example, the robot capability parameters 204A, the touch parameters 204B, the control parameters 204C, and the like) for the HMI device 104. In some embodiments, the user input may be received based on the control of the rendering of the electronic UI 114. Examples of the I/O device 306 may include, but are not limited to, a touch screen, a keyboard, a mouse, a joystick, a microphone, a display device, and a speaker. Examples of the I/O device 306 may further include braille I/O devices, such as braille keyboards and braille readers.

The I/O device 306 may include the electronic UI 114. The electronic UI 114 may include suitable logic, circuitry, and interfaces that may be configured to receive inputs from the controller 302 to render, on a display screen, UI elements (for example, first UI elements, second UI elements, etc.), the user-feedback associated with the user-interaction of the HMI device 104, and modified parameters. In at least one embodiment, the electronic UI 114 may be at least one of a resistive touch screen, a capacitive touch screen, or a thermal touch screen. The electronic UI 114 may be realized through several known technologies such as, but not limited to, at least one of a Liquid Crystal Display (LCD) display, a Light Emitting Diode (LED) display, a plasma display, or an Organic LED (OLED) display technology, or other display devices.

The actuators 310 may receive signals from the controller 302 and execute the corresponding physical movement. There may be different type of actuators 310 used in the HMI device 104, depending on the load associated with factors such as, but not limited to force, torque, speed of operation, precision, accuracy, and power consumption. The actuators 310 may, for example, receive inputs from the user 106A/operator 106B to control the operation of the HMI device 104 and the actuator 310 may be operated based on the control commands received from the controller 302.

The sensors 308 may measure some attribute of a surrounding environment and convert the measured attribute into a signal that can be read or interpreted by the HMI device 104. The sensors 308 may help robots to understand and measure the geometric and physical properties of objects in their surrounding environment, such as position, orientation, velocity, acceleration, distance, size, force, moment, temperature, luminance, weight, etc. The sensors 308 are essential for robots to operate with remarkable precision and efficiency, and to interact safely and effectively with their environment and with other machines. The sensors 308 used in the HMI device 104 may include, but not limited to proprioceptive sensors, exteroceptive sensors, light sensors, and sound sensors.

The network interface 312 may include suitable logic, circuitry, and interfaces that may be configured to facilitate communication between the HMI device 104, the electronic device 102, and the server 108, via the communication network 112. The network interface 312 may be implemented by use of various known technologies to support wired or wireless communication of the HMI device 104 with the communication network 112. The network interface 312 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry.

The network interface 312 may be configured to communicate via wireless communication with networks, such as the Internet, an Intranet, or a wireless network, such as a cellular telephone network, a wireless local area network (LAN), a short-range communication network 312, and a metropolitan area network (MAN). The wireless communication may use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), $5^{th}$ Generation (5G) New Radio (NR), code division multiple access (CDMA), time division multiple access (TDMA), Bluetooth, Wireless Fidelity (Wi-Fi) (such as IEEE 802.11a, IEEE 802.11b, IEEE 802.11g or IEEE 802.11n), voice over Internet Protocol (VoIP), light fidelity (Li-Fi), Worldwide Interoperability for Microwave Access (Wi-MAX), a near field communication protocol, and a wireless pear-to-pear protocol.

Figure 4:
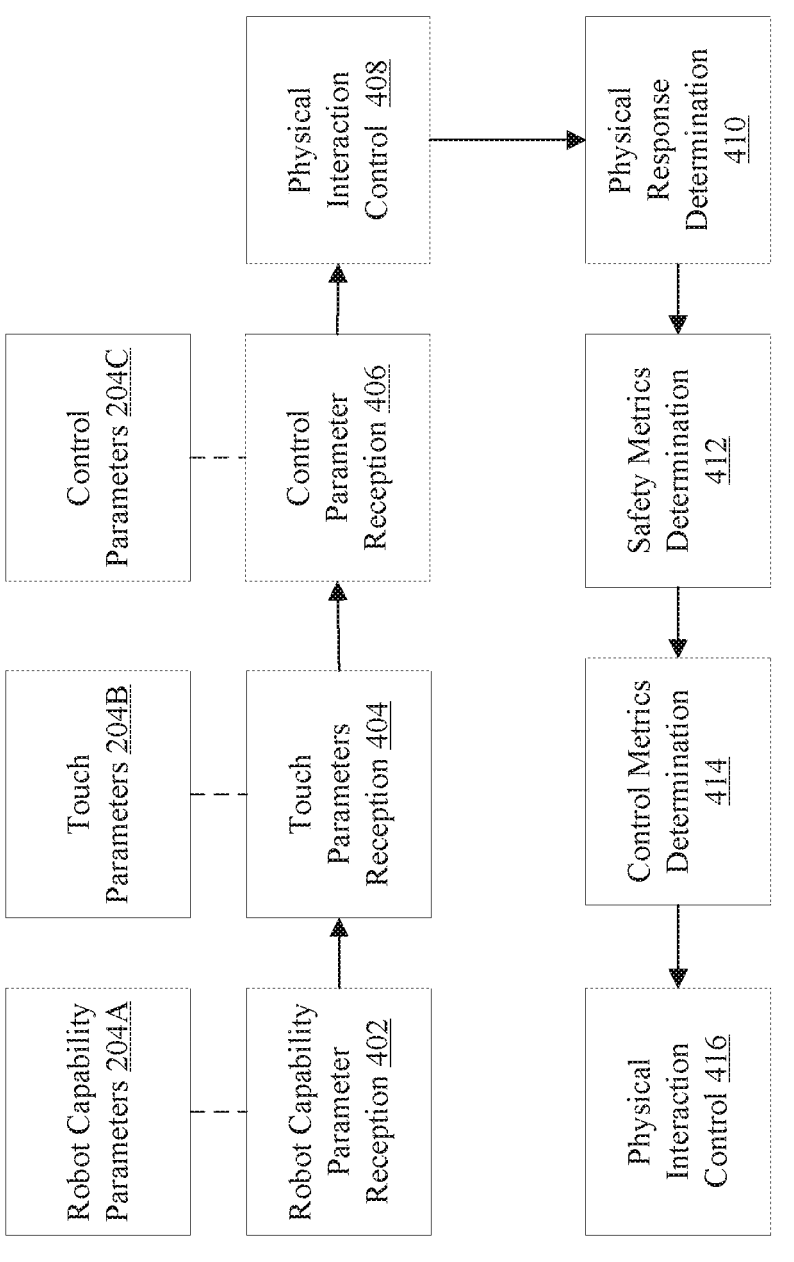
FIG. 4 is a diagram that illustrates a processing pipeline for safety and control enhancement in tele-operated physical human-robot interactions, in accordance with an embodiment of the disclosure.

FIG. 4 is a diagram that illustrates a processing pipeline for safety and control enhancement in the tele-operated physical human-robot interactions, in accordance with an embodiment of the disclosure. With reference to FIG. 4, there is shown an exemplary execution pipeline 400 for safety and control enhancement in the tele-operated physical human-robot interactions of the HMI device 104 and the user 106A. The execution pipeline 400 may include operations 402 to 416 executed by a computing device, such as the electronic device 102 of FIG. 1 or the circuitry 202 of FIG. 2.

At 402, an operation for reception of robot capability parameters may be executed. The circuitry 202 of the electronic device 102 may be configured to receive the robot capability parameters 204A associated with the HMI device 104. The robot capability parameters 204A may include the form factor parameter of the HMI device 104, the level of autonomy of the HMI device 104, the degree of freedom of the HMI device 104 and the like. The form factor parameter of the HMI device 104 may refer, but is not limited to a size, a shape, and a physical design of the HMI device 104 or a part of the HMI device 104 that is configured to interact with the user 106A. The level of autonomy of the HMI device 104 may include the degree of independence and self-governance in various contexts, such as psychology, robotics, and social structures associated with the HMI device 104. The degree of freedom in the HMI device 104 may refer to a range of movements or control actions that the user 106A may perform with the HMI device 104, for example, touch screen panels, joysticks and trackballs, 3D control console, voice-controlled interfaces, and the like. The touch screen panels may include multi-touch capabilities that allows users to interact with the HMI device 104, for example, the interaction may include, but is not limited to, pinch, zoom, and swipe. The joysticks and trackballs may include a feature of moving in multiple directions, translating to multiple degrees of freedom for precise control in navigating through interfaces. The 3D control console may detect movements along, for example, three axes (X, Y, and Z) and rotations around those axes, offering six degrees of freedom. The voice-controlled interfaces may use commands through speech, which can be considered a degree of freedom as it provides an alternative method of interaction beyond physical controls.

At 404, an operation for reception of touch parameters may be executed. The circuitry 202 may be configured to receive the touch parameters 204B associated with a physical-interaction of the HMI device 104 and a user (e.g., the user 106A). The touch parameters 204B may include, but are not limited to, orientation, speed (for example, 1 m/s), force (for example, 15N), time duration (for example, 5 seconds), and a contact zone between the HMI device 104 and the user 106A. The orientation of the HMI device 104 may use a combination of rotations around the X, Y, and Z axes to achieve a desired orientation. This could be represented, for example, by a rotation matrix or a rotation vector in a robot control system associated with the HMI device 104. Additionally, the HMI device 104, like collaborative robots, may use an orientation vector based on the axis-angle representation, which involves rotating around a specific vector by a certain angle. Another example is the use of RPY (roll, pitch, yaw) values and are often used in the interfaces of robots, which uses a ZY'X" convention for Euler angles. The contact zone may refer to the area where physical interaction occurs between the HMI device 104 and user 106A. An example of a contact zone may be a scenario where a collaborative HMI device and user 106A work together to carry a heavy object. The collaborative HMI device and user 106A may include sensors to detect a user's presence and apply the appropriate force to assist with the lifting task, ensuring safety and efficiency in the shared workspace. Another example is the use of dynamic safety zones in industrial settings, where a safety-certified camera monitors the distance between HMI device 104 and user 106A. If the user 106A enters a predefined detection zone, the HMI device 104 may perform a safety-rated monitored stop to prevent accidents.

At 406, an operation for reception of control parameters may be executed. The circuitry 202 may be configured to receive the control parameters 204C associated with the operator 106B of the HMI device 104 to control the physical-interaction of the HMI device 104 with a user (e.g., the user 106A). The control parameters 204C associated with the operator 106B may include, but are not limited to, operator-control freedom parameters associated with the HMI device 104, a touch-based feedback from the patient/user 106A, and a user interface control associated with the operator 106B. The operator-control freedom parameters in the HMI device 104 may refer to the various degrees of freedom that an operator has when controlling the HMI device 104. The operator-control freedom parameters define the flexibility and range of motion that the robot can achieve under human control, for example, degrees of freedom, force/torque sensing, velocity and position control, admittance and impedance control, and the like. The touch-based feedback from the user 106A in the HMI 104 refers to the tactile response or sensation that the user 106A experiences when interacting with the HMI device 104. For example, the touch-based HMI device 104 might be used by the user 106A (such as a patient) at hospitals or nursing homes, where patients can input their symptoms or discomfort levels. The HMI device 104 may provide a gentle vibration or other tactile response to confirm the patient's input, enhancing the user experience and ensuring that the patient's entries have been registered correctly. The user interface control associated with the operator 106B may correspond to user inputs including instructions to control the HMI device 104. The user inputs may be received through the electronic UI 114.

At 408, an operation for physical interaction control may be executed. The circuitry 202 of the electronic device 102 may be configured to control the physical interaction of the HMI device 104 based on the received robot capability parameters 204A, the received touch parameters 204B, and the received control parameters 204C. The circuitry 202 may determine instructions to control the physical interaction of the HMI device 104 based on the received robot capability parameters 204A, the received touch parameters 204B, and the received control parameters 204C. For example, the received robot capability parameters 204A may indicate that the HMI device 104 may be required to have 6 degrees of freedom. The received touch parameters 204B may indicate that the HMI device 104 may be required to apply 1 N of force for 1 minute duration, at a certain body portion of the user 106A. Further, the received control parameters 204C may indicate that the HMI device 104 may be required to enable the operator 106B to manually control the HMI device 104 across at least 3 degrees of freedom at a time. Accordingly, the circuitry 202 may determine the corresponding instructions to control the HMI device 104. The circuitry 202 may transmit the determined instructions to the HMI device 104, which may look-up an instruction table in the memory 304 to interpret the instructions and convert the interpreted instructions to corresponding control commands.

The HMI device 104 may execute the corresponding control commands and the various components of the HMI device 104 may be accordingly controlled. Also, the physical interaction of the HMI device 104 may be further controlled based on the safety metrics and the control metrics, as described further, for example, at 416.

At 410, an operation for determination of physical response of the user may be executed. The circuitry 202 may be configured to determine a physical response of the user 106A, based on the control of the physical interaction of the HMI device 104. The physical response of the user 106A may be determined based on the control of the physical interaction of the HMI device 104. The physical response of the user 106A may include, but is not limited to, a body movement of the user 106A, a gaze of the user 106A, a verbal response of the user 106A, and a facial response of the user 106A. The controller 302 may determine the physical response of the user 106A, based on use of the sensors 308. The circuitry 202 may receive information related to the determined physical response of the user 106A from the controller 302. In addition, or alternatively, the electronic device 102 may include sensors (not shown in FIG. 2), such as an image capture device, a microphone, and the like. In such a case, the circuitry 202 may control the sensors of the electronic device 102 to determine the physical response of the user 106A.

The HMI device 104 may be configured to operate based on a co-design experimental procedure with at least two iterations, a user interface that may help users to select robot settings, and evaluation tools that may measure the interaction experience of the users with the robot using both numbers and words with an emphasis on safety and comfort. Therefore, both qualitative measures and quantitative measures may be used to enhance user experience of the HMI devices focusing on perceived safety and comfort. The safety and control of the HMI device 104 in performing the relevant action involving an end-user may be enhanced based on the user experience and physical response based iterative control of the HMI device 104.

At 412, an operation for determination of safety metrics associated with the user may be executed. The circuitry 202 may be configured to determine the safety metrics associated with the user 106A, based on the determined physical response, the received robot capability parameters 204A, and the received touch parameters 204B. The safety metrics may include, but is not limited to, the trust level of the user 106A associated with the HMI device 104, the comfort level of the user 106A associated with the HMI device 104, and the safety level of the user 106A associated with the HMI device 104. For example, the physical response of the user 106A may indicate that the user 106A has relaxed facial expressions. Further, the robot capability parameters 204A may indicate that the HMI device 104 may have a portable form factor that may be of a size of a hand of the user 106A. The touch parameters 204B may indicate that the HMI device 104 may have applied a force of 1 N, for 1 minute, at an arm region of the user 106A to sooth a pain of the user 106A. In current scenario, the circuitry 202 may determine that the comfort level of the user 106A may be high (e.g., close to "1", assuming that the comfort level ranges from "0" to "1", where "1" is the highest and "0" is the lowest).

At 414, an operation for determination of control metrics associated with the operator may be executed. The circuitry 202 may be configured to determine the control metrics associated with the operator 106B, based on the received robot capability parameters 204A, and the received control parameters 204C. The control metrics may include, but is not limited to, a physical load on the operator 106B, the mental load on the operator 106B, the level of control of the operator 106B, the level of awareness of the operator 106B, and the task performance by the HMI device 104. Also, the electronic device 102 may receive user-background parameters and operator-background parameters associated with the HMI device 104. For example, the robot capability parameters 204A may indicate that the HMI device 104 has a form factor of a portable device and has a high level of autonomy. Further, the control parameters 204C may indicate that the HMI device 104 may enable the operator 106B to manually control the HMI device 104 across at least 3 degrees of freedom at a time. In one scenario, the circuitry 202 may determine that the physical load and the mental load on the operator 106B may be less. The physical and mental loads may be less as the HMI device 104 may be of a small size that may fit inside a hand of the operator 106B, the HMI device has a high level of autonomy and requires less supervision, and further manual control of the HMI device 104 is easy across 3 degrees of freedom.

At 416, an operation for control of the physical interaction of the HMI device may be executed. The circuitry 202 may be configured to control the physical interaction of the HMI device 104 further based on the determined safety metrics and the determined control metrics. For example, the safety metrics may indicate that the trust level of the user 106A on the HMI device 104 is low (for example, less than 0.3). Further, the control metrics may indicate that the physical and mental load on the operator 106B may be high. In such a scenario, the circuitry 202 may determine that the HMI device 104 may not be comfortable to use for the user 106A and may be difficult to control for the operator 106B. Accordingly, the circuitry 202 may generate instructions to slow down a speed of the HMI device 104 and reduce a force applied by the HMI device 104. The circuitry 202 may transmit the generated instructions to the HMI device 104. The controller 302 of the HMI device 104 may receive the generated instructions and look-up an instruction table stored in the memory 304 to determine control commands corresponding to the generated instructions. Based on the determined control commands, the controller 302 may control the components of the HMI device 104 and accordingly control the physical interaction of the HMI device 104.

Figure 5:
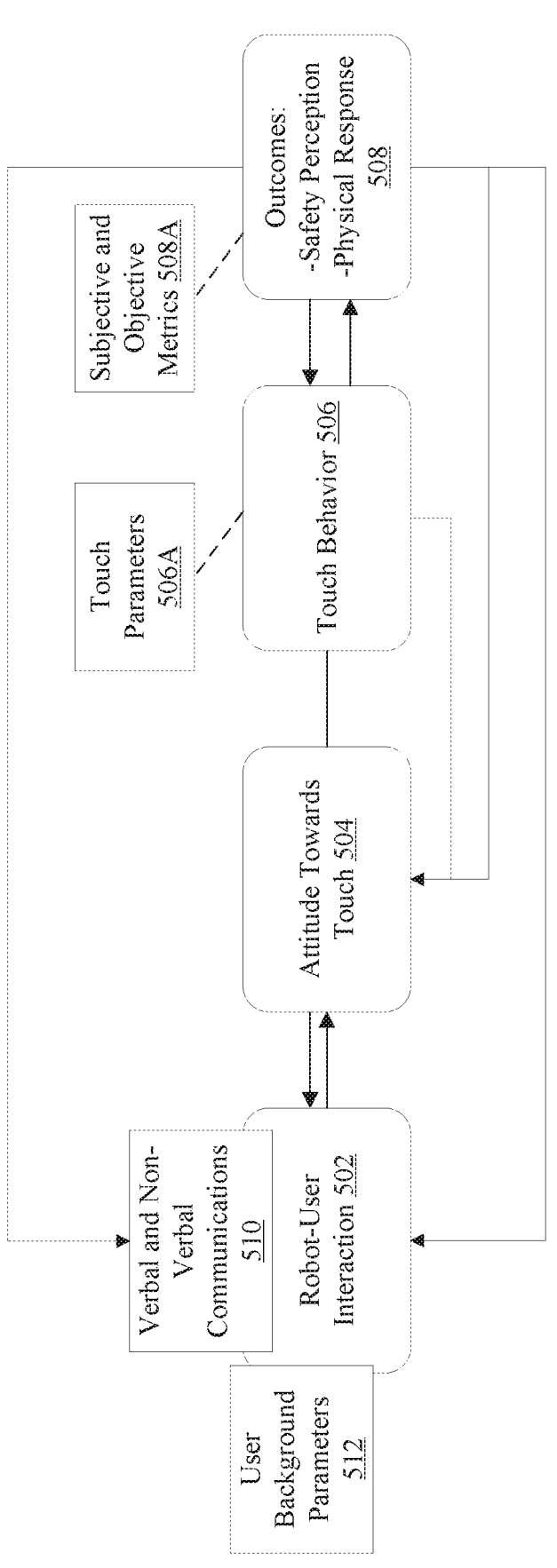
FIG. 5 is a diagram that illustrates an exemplary scenario of a tele-operated human-robot interaction, in accordance with an embodiment of the disclosure.

FIG. 5 is a diagram that illustrates an exemplary scenario of a tele-operated human-robot interaction, in accordance with an embodiment of the disclosure. FIG. 5 is explained in conjunction with elements from FIGS. 1, 2, 3 and 4. With reference to FIG. 5, there is shown an exemplary scenario 500 of a tele-operated human-robot interaction. The scenario 500 may include various operations performed by the HMI device 104 and/or the electronic device 102. For example, the operations may include, but are not limited to, an operation for a robot-user interaction 502, an operation for determination of an attitude towards touch 504, an operation for determination of a touch behavior 506, and an operation for determination of outcomes 508 (e.g., safety perception and physical responses). The scenario 500 may further include user-background parameters 512, verbal and non-verbal communications 510, touch parameters 506A, and subjective and objective metrics 508A.

At 502, the operation of robot-user interaction may be performed. The user 106A may interact with the robot (e.g., the HMI device 104) and the interactions may be recorded by the HMI device 104 and/or the electronic device 102. The user background parameters (e.g., the user-background parameters 512) may be used while performing the robot-user interaction. For example, behavior of the HMI device 104 may be configured based on the user-background parameters 512. For example, in case of aged users, the HMI device 104 may apply low amount of force and may apply the force on smaller portions of the body to ensure comfort for the user. The physical interaction of the HMI device 104 may be controlled based on the robot capability parameters 204A, touch parameters 204B, and control parameters 204C. The electronic device 102 of the disclosure may enable a human-robot interaction to gather insights and ground robot design choices when investigating physical human-robot interaction scenarios, especially in the tele-operated health care that involve instrumental touch interactions. In essence, the outcomes of HRI may be pivotal for those creating future tele-operated healthcare robots. It emphasizes the importance of understanding the nuances of physical interactions between humans and robots to design systems that are effective, safe, and user-friendly. This may be particularly relevant in healthcare settings where precision and reliability are critical.

In an embodiment, the robots can receive a variety of inputs to interact with humans and their environment, through both verbal and non-verbal communications (e.g., the verbal and non-verbal communications 510). For example, the verbal inputs may be received as spoken commands from a user based on speech recognition or natural language processing (NLP) techniques. The non-verbal inputs may be received based on visual cues, tactile sensors, motion sensors, environmental sensors, and the like. For example, the robot-patient interaction involving user inputs may be used in some hospitals to interact with patients. The HMI device 104 may be designed to recognize human emotions and engage in conversations. It can be programmed to perform tasks like greeting visitors, providing patient information, and even leading patients to different departments within the hospital. Patients and staff can interact with the HMI device 104 using a touchscreen tablet to input commands or select options for assistance.

At 504, the operation for determination of the attitude towards touch may be performed based on the robot-user interaction. For example, the HMI device 104 and the user 106A may work together to carry a heavy object. The HMI device 104 may include sensors to detect the presence of the user 106A and apply an appropriate force to assist with the lifting task, ensuring safety and efficiency in the shared workspace. Another example is the use of dynamic safety zones in industrial settings, where a safety-certified camera monitors the distance between the HMI device 104 and user 106A. If the user 106A enters a predefined detection zone, the HMI device 104 may perform a safety-rated monitored stop to prevent accidents At 506, the operation for determination of the touch behavior may be performed. The touch behavior may correspond to the physical response of the user 106A. The physical response of the user 106A may include the body movement, the gaze, the verbal response, and the facial response of the user 106A, and the like. The control metrics may include the physical load on the operator 106B, the mental load on the operator 106B, the level of control of operator 106B, the level of awareness of the operator 106B, the task performance by the HMI device 104, and the like. The touch behavior may be determined based on the touch parameters 204B. The touch parameters may include but not limited to orientation, speed (for example, 1 m/s), force (for example, 15N), time duration (for example, 5 seconds) and a contact zone between the HMI device 104 and the user 106A. The orientation of the HMI device 104 may use a combination of rotations around the X, Y, and Z axes to achieve a desired orientation. This could be represented by a rotation matrix or a rotation vector in the robot's control system. Additionally, the HMI device 104, like collaborative robots, may use an orientation vector based on the axis-angle representation, which involves rotating around a specific vector by a certain angle. Another example is the use of RPY (roll, pitch, yaw) values and are often used in the interfaces of robots, which uses a ZY'X'' convention for Euler angles.

At 508, the operation for determination of the outcome may be performed, based on the touch behavior. The outcomes may include the safety and comfort perceptions and the physical response of the user 106A. The safety metrics associated with the user 106A may be determined based on the determined response, the received robot capability parameters 204A, and the control parameters 204C. The safety metrics may include, but is not limited to, the trust level of the user 106A associated with the HMI device 104, the comfort level of the user 106A associated with the HMI device 104, and the safety level of the user 106A associated with the HMI device 104. The HMI device 104 may include a two-step co-design experimental procedure, a user interface that helps users select robot settings, and evaluation tools that measure the interaction experience of the user 106A with the robot using both numbers and words with an emphasis on safety and comfort. Therefore, both qualitative measures and quantitative measures may be used to enhance user experience of the HMI devices 104 focusing on perceived safety and comfort. This may further enhance safety and control of the HMI device 104 in performing the relevant action involving an end-user.

As shown in FIG. 5, the touch behavior (denoted by 506) may be affected by the outcomes (denoted by 508), and vice versa. The attitude towards touch (denoted by 504) may also be affected by the touch behavior (denoted by 506) and the outcomes (denoted by 508). The robot-user interaction (denoted by 502) may be influenced by the outcomes (denoted by 508) and the attitude towards touch (denoted by 504). Also, the verbal and non-verbal communications (denoted by 510) may be affected by the outcomes (denoted by 508). Hence, each stage of this scenario may be provided a feedback loop from the outcomes (denoted by 508). The control of the HMI device 104 may be based on the outcomes, such as the safety perception and the physical response of the user 106A. It should be noted that the scenario 500 of FIG. 5 is for exemplary purposes and should not be construed to limit the scope of the disclosure.

Figure 6:
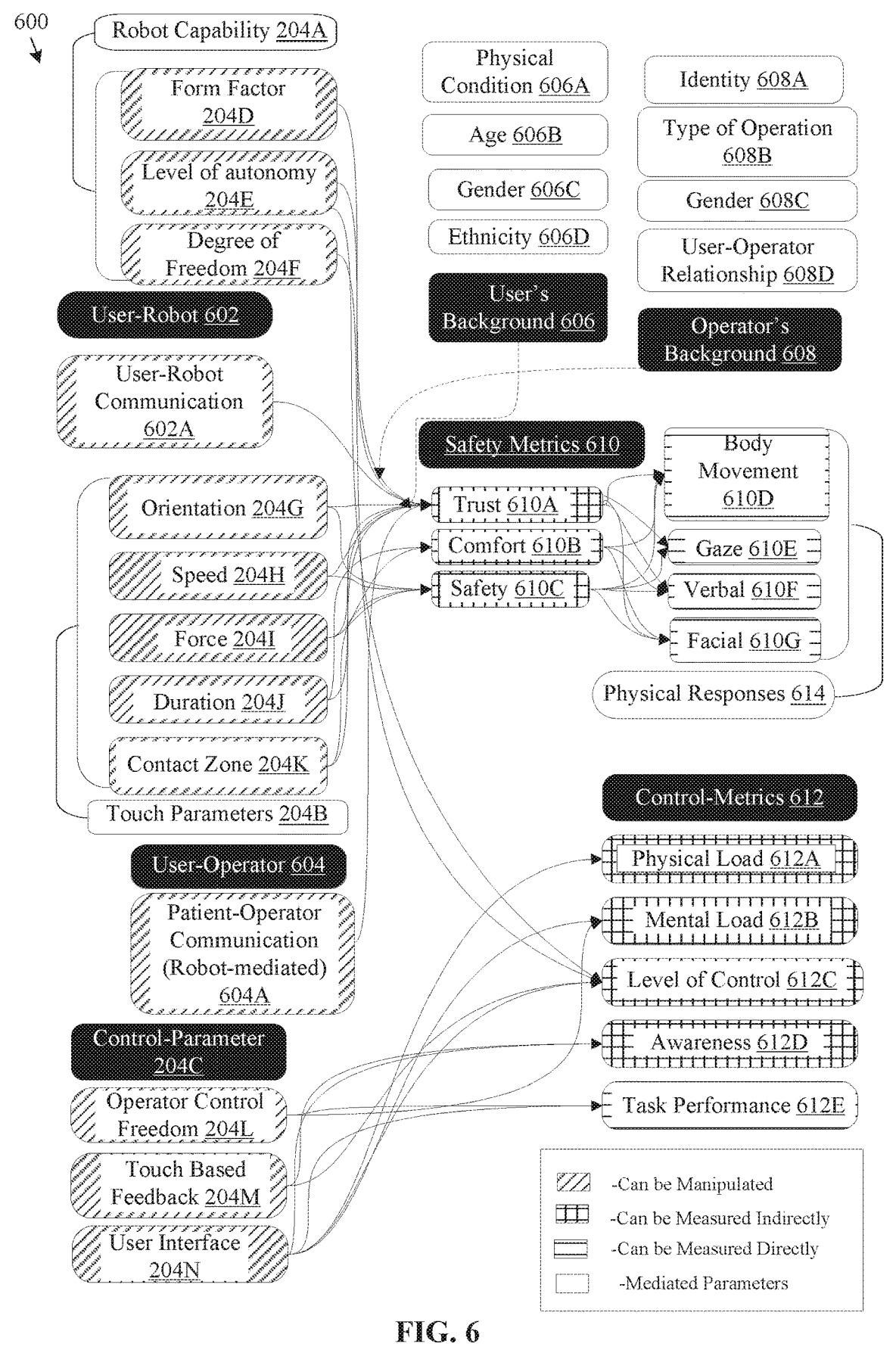

FIG. 6 is a diagram that illustrates an exemplary scenario for tele-operated human-robot interaction to control physical interaction of the HMI device, in accordance with an embodiment of the disclosure. With reference to FIG. 6, there is shown the exemplary scenario 600 for tele-operated human-robot interaction. The exemplary scenario 600 may include various parameters which may affect the determination of the safety perspective of the user 106A. The various parameters may include, for example, the robot capability parameters 204A, the touch parameters 204B, the control parameters 204C, a user-robot parameter (denoted by 602), a user-operator parameter (denoted by 604), user's background parameters (denoted by 606), operator's background parameters (denoted by 608), safety metrics (denoted by 610) of the user 106A, control metrics (denoted by 612), and the like.

The robot capability parameters 204A may include, but are not limited to, a form factor 204D, a level of autonomy 204E, and a degree of freedom 204F. The user background parameters 606 may include, but are not limited to, physical conditions 606A, an age 606B, a gender 606C, and an ethnicity 606D of the user 106A. The operator background parameters 608 may include, but are not limited to, an identity 608A, a type of operation 608B, a gender 608C, and a user-operator relationship 608D.

The user-robot parameter 602 may include user-robot communication 602A. The user-robot communication 602A may correspond to first communication metrics associated with the user 106A and the HMI device 104. The circuitry 202 may determine the first communication metrics based on a type and amount/frequency of feedback received by the HMI device 104 from the user 106A. The user-operator parameter 604 may include patient-operator communication (robot-mediated) 604A. The patient-operator communication (robot-mediated) 604A may correspond to second communication metrics associated with the user 106A and the operator 106B. The circuitry 202 may be configured to determine the second communication metrics based on a type and amount/frequency of communication between the user 106A and the operator 106B, through robot mediated user interfaces (e.g., the electronic UI 114) and/or the electronic device 102. In an embodiment, a trust level of the user 106A of the HMI device 104 may be correlated with the determined first communication metrics and the determined second communication metrics. Examples of types of feedback may include tactile/haptic feedback, voice commands, gesture-based commands, and the like. The amount/frequency of feedback/communication may be indicative of how much and how often there is a feedback/communication from the user 106A. For example, if the user 106A provides a frequent tactile feedback/communication, the trust level of the user 106A may not be high; however, if the user 106A provides less frequent feedback or communicates occasionally, the trust level of the user 106A may be high.

The touch parameters 204B may include, but are not limited to, an orientation 204G, a speed 204H, a force 204I, a duration 204J, and a contact zone 204K. The safety metrics 610 may include, but are not limited to, a trust 610A, a comfort 610B, a safety 610C, and physical responses 614 of the user 106A, which may include, but not limited to, a body movement 610D, a gaze 610E, a verbal response 610F, and a facial response 610G. The control parameters 204C may include, but are not limited to, an operator control freedom 204L, a touch based feedback 204M, and a user interface 204N. The control metrics 612 may include, but are not limited to, a physical load 612A, a mental load 612B, a level of control 612C, an awareness 612D, and a task performance 612E.

The robot capability parameters 204A, such as the form factor 204D and the level of autonomy 204E, may be correlated with the trust 610A of the safety metrics 610. The level of autonomy 204E may be used to determine trust 610A and the level of control 612C of the control metrics 612. The degree of freedom 204F of the robot capability parameters 204A may be correlated with the level of control 612C of the control metrics 612. The user-robot communication 602A may be correlated with the trust 610A of the safety metrics 610. The orientation 204G of the touch parameters 204B may be correlated with the trust 610A and the safety 610C. The speed 204H may be correlated with the comfort 610B and the safety 610C. The force 204I may be correlated with the comfort 610B and the safety 610C. The duration 204J may be correlated with the trust 610A and the comfort 610B. The contact zone 204K may be correlated with the trust 610A and the safety 610C. The patient-operator communication 604A may be correlated with the trust 610A. The operator control freedom 204L may be correlated to the mental load 612B, and the task performance 612E. The touch based feedback 204M may be correlated to the level of control 612C and the awareness 612D. The user interface 204N may be correlated to the physical load 612A, the mental load 612B, the level of control 612C, awareness 612D, and the task performance 612E.

Further, the user background parameters 606 may act as mediated parameters for the various parameters, for instance, but not limited to, the touch parameters 204B. The operator background parameters 608 may act as mediated parameters for the various parameters, for instance, but not limited to, the touch parameters 204B. Further, the safety metrics 610, such as the trust 610A, may be directly correlated with the physical responses 614 of the user 106A, including but not limited to, the body movement 610D, the gaze 619E, the verbal response 610F, and the facial response 610G of the user 106A. The comfort 610B may be correlated to the body movement 610D, the verbal response 610F, and the facial response 610G of the user 106A. The safety 610C may be correlated to the body movement 610D, the gaze 619E, the verbal response 610F, and the facial response 610G of the user 106A.

In an embodiment, the parameters, for example, the form factor 204D, the level of autonomy 204E, the degree of freedom 204F, the user-robot communication 602A, the orientation 204G, the speed 204H, the force 204I, the duration 204J, the contact zone 204K, the patient-operator communication 604A, the operator control freedom 204L, the touch based feedback 204M, and user interface 204N may be manipulatable parameters. The parameters, for example, the trust 610A, the comfort 610B, the safety 610C, the physical load 612A, the mental load 612B, the level of control 612C, and the awareness 612D may be measured indirectly based on the manipulatable parameters. The parameters, for example, the body movement 610D, the gaze 610E, the verbal response 610F, the facial response 610G, and the task performance 612E may be measured directly based on the manipulatable parameters. It should be noted that the scenario 600 of FIG. 6 is for exemplary purposes and should not be construed to limit the scope of the disclosure.

FIG. 7 is a flowchart that illustrates operations of an exemplary method for safety and control enhancement in tele-operated physical human-robot interactions, in accordance with an embodiment of the disclosure. FIG. 7 is explained in conjunction with elements from FIGS. 1, 2, 3, 4, 5, and 6. With reference to FIG. 7, there is shown a flowchart 700. The flowchart 700 may include operations from 702 to 716 and may be implemented by the electronic device 102 of FIG. 1. The flowchart 700 may start at 702 and proceed to 704.

At 704, the robot capability parameters 204A associated with the HMI device 104 may be received. The circuitry 202 may be configured to receive the robot capability parameters 204A associated with the HMI device 104. The robot capability parameters 204A may include, but are not limited to, the form factor parameter of the HMI device 104, the level of autonomy of the HMI device 104, the degree of freedom of the HMI device 104 and the like. The form factor parameter of the HMI device 104 may refer, but is not limited to size, shape, and physical design. The level of autonomy of the HMI device 104 may include the degree of independence and self-governance in various contexts, such as psychology, robotics, and social structures associated with the HMI device 104. The degree of freedom in the HMI device 104 may refer to a range of movements or control actions that the user 106A may perform with the HMI device 104, for example, touch screen panels, joysticks and trackballs, 3D control console, voice-controlled interfaces, and the like. The reception of the robot capability parameters is described further, for example, in FIG. 4 (at 402).

At 706, the touch parameters 204B associated with the physical-interaction of the HMI device 104 and user 106A may be received. The circuitry 202 may be configured to receive the touch parameters 204B associated with the physical-interaction of the HMI device 104 and user 106A. The touch parameters 204B may include, but is not limited to, the orientation, speed, force, time duration, contact zone and so on. The reception of the touch parameters is described further, for example, in FIG. 4 (at 404).

At 708, the control parameters 204C associated with the operator 106B and the HMI device 104 may be received, to control the physical interaction of the HMI device 104. The circuitry 202 may be configured to receive the control parameters 204C associated with the operator 106B of the HMI device 104, to control the physical-interaction of the HMI device. The control parameters 204C associated with the operator 106B include, but are not limited to, operator-control freedom parameters associated with the HMI device 104, touch-based feedback from the patient/user 106A, and user interface control associated with the operator 106B. The operator-control freedom parameters in the HMI device 104 may refer to the various degrees of freedom (DOF) that an operator has when controlling the HMI device 104. The touch-based feedback from the user 106A in the HMI 104 refers to the tactile response or sensation that the user 106A experiences when interacting with the HMI device 104. The reception of the control parameters is described further, for example, in FIG. 4 (at 406).

At 710, the physical interaction of the HMI device 104 may be controlled based on the based on received robot capability parameters 204A, received touch parameters 204B, and received control parameters 204C. The circuitry 202 may be configured to control the physical interaction of the HMI device 104 based on the received robot capability parameters 204A, the received touch parameters 204B, and the received control parameters 204C. The physical inter-action using various parameters, such as, but not limited to, the robot capability parameters 204A, the touch parameters 204B, and the control parameters 204C, may involve under-standing factors influencing movement and interactions of the HMI device 104. For instance, HMI device 104 may be programmed to respond to the physical human interventions by adjusting its trajectory. The parameters (such as the control parameters 204C) may be set by the user 106A or the operator 106B.

In an embodiment, there may be different types of HMI device 104 or robots and interfaces, depending on the control and programming approach, the environment and task, and the human-machine interaction. For example, some robots may use collaborative robots that can perform complex tasks in various environments, while others may use manual robots that require complete human intervention for their operation. Some interfaces may use a robot oper-ating system (ROS), which may be a framework that pro-vides a painless entry point for nonprofessionals in the field of programming robots. The control of the physical inter-action of the HMI device is described further, for example, in FIG. 4 (at 408).

At 712, the physical response of the user 106A may be determined, based on the control of the physical interaction of the HMI device 104. The circuitry 202 may be configured to determine the physical response of the user 106A, based on the control of the physical interaction of the HMI device 104. The physical response may be determined based on tracking of user inputs, system responses, and the overall performance of the interaction process. To effectively record the physical responses of the user 106A, continuous user feedback may be essential for refining the HMI device 104. For example, the electronic device 102 and/or HMI device 104 may include sensors, such as image capture devices, to capture images of the user 106A, while the HMI device 104 is interacting with the user 106A. Based on the captured images, physical response of the user 106A, such as the facial expressions and body movement of the user 106A, may be determined. The determination of the physical response of the user is described further, for example, in FIG. 4 (at 410).

At 714, safety metrics associated with the user 106A may be determined, based on the physical response, the robot capability parameters 204A, and the touch parameters 204B. The circuitry 202 may be configured to determine the safety metrics associated with the user 106A, based on the deter-mined physical response, the received robot capability parameters 204A, and the received touch parameters 204B. For example, if the user 106A has a facial expression that indicates that the user 106A is comfortable and the HMI device 104 is a portable hand-held device that applies a small amount of force on a body portion of the user 106A to alleviate a pain of the user 106A, the safety metrics may have a high value (e.g., a value close to "1"). The determi-nation of the safety metrics associated with the user is described further, for example, in FIG. 4 (at 412).

At 716, the control metrics associated with the operator 106B may be determined based on the received robot capability parameters 204A and the received control param-eters 204C. The circuitry 202 may be configured to deter-mine control metrics associated with the operator 106B, based on the received robot capability parameters 204A and the received control parameters 204C. The control metrics may include, but is not limited to, a physical load on the operator 106B, the mental load on the operator 106B, the level of control of the operator 106B, the level of awareness of the operator 106B, and the task performance by the HMI device 104. Also, the electronic device 102 may receive user-background parameters and operator-background parameters associated with the HMI device 104. The deter-mination of the control metrics associated with the user is described further, for example, in FIG. 4 (at 414).

At 718, the physical interaction of the HMI device 104 may be controlled, further based on the determined safety metrics and the determined control metrics. The circuitry 202 may be configured to control the physical interaction of the HMI device 104, further based on the determined safety metrics and the determined control metrics. For example, the safety metrics may indicate that the trust level of the user 106A on the HMI device 104 is low (for example, less than 0.3). Further, the control metrics may indicate that the physical and mental load on the operator 106B may be high. In such a scenario, the circuitry 202 may determine that the HMI device 104 may not be comfortable to use for the user 106A and may be difficult to control for the operator 106B. Accordingly, the circuitry 202 may generate instructions to slow down a speed of the HMI device 104 and reduce a force applied by the HMI device 104. In an example of a health-care scenario, a robot and user interaction may be observed. These robots may assist users 106A who are recovering from injuries or surgeries. For instance, a robotic arm may help a patient perform physical therapy exercises. The robot may adjust its support based on the user's force and movement, providing just enough assistance to help the patient complete the movement without taking over completely. This allows the user 106A to attain the safety and control associated with the HMI device 104. The HMI device 104 may include, but not limited to social HMI devices, collaborative HMI device, prosthetics and exoskeletons, teleoperated HMI devices, and the like. Control may pass to end.

Although the flowchart 700 is illustrated as discrete operations, such as 704, 706, 708, 710, 712, 714, 716, and 718 the disclosure is not so limited. Accordingly, in certain embodiments, such discrete operations may be further divided into additional operations, combined into fewer operations, or eliminated, depending on the implementation without detracting from the essence of the disclosed embodiments.

Various embodiments of the disclosure may provide a non-transitory computer-readable medium and/or storage medium having stored thereon, computer-executable instructions executable by a machine and/or a computer to operate an electronic device (for example, the electronic device 102 of FIG. 1). Such instructions may cause the electronic device 102 to perform operations that may include receiving robot capability parameters (e.g., the robot capability parameters 204A) associated with a human-machine interaction (HMI) device (e.g., the HMI device 104) and receiving touch parameters (e.g., the touch parameters 204B) associated with a physical-interaction of the HMI device 104 and a user (e.g., the user 106A). The operations may further include reception of control parameters (e.g., the control parameters 204C) associated with an operator (e.g., the operator 106B) of the HMI device 104 to control the physical-interaction of the HMI device 104. The operations may further include control of the physical interaction of the HMI device 104 based on the received robot capability parameters 204A, the received touch parameters 204B, and the received control parameters 204C. The operations may further include determination of a physical response of the user 106A, based on the control of the physical interaction of the HMI device 104 and determination of safety metrics associated with the user 106A, based on the determined physical response, the received robot capability parameters 204A, and the received touch parameters 204B. Also, the operations may further include determination of control metrics associated with the operator 106B, based on the received robot capability parameters 204A, and the received control parameters 204C and further controlling the physical interaction of the HMI device 104, further based on the determined safety metrics and the determined control metrics.

Exemplary aspects of the disclosure may provide an electronic device (such as the electronic device 102 of FIG. 1) that includes circuitry (such as the circuitry 202). The circuitry 202 may be configured to receive the robot capability parameters 204A associated with the HMI device 104 and receive the touch parameters 204B associated with the physical-interaction of the HMI device 104 and the user 106A. Further the circuitry 202 may be configured to receive control parameters 204C associated with the operator 106B of the HMI device 104 to control the physical-interaction of the HMI device 104 based on the received robot capability parameters 204A, the received touch parameters 204B, and the received control parameters 204C. Further the circuitry 202 may be configured to determine a physical response of the user 106A, based on the control of the physical inter-action of the HMI device 104 and further determine safety metrics associated with the user 106A, based on the determined physical response, the received robot capability parameters 204A, and the received touch parameters 204B. Also, the circuitry 202 may be configured to determine control metrics associated with the operator 106B, based on the received robot capability parameters 204A, and the received control parameters 204C and further configured to control the physical interaction of the HMI device 104, further based on the determined safety metrics and the determined control metrics.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted for carrying out the methods described herein may be suited. A combination of hardware and software may be a general-purpose computer system with a computer program that, when loaded and executed, may control the computer system such that it carries out the methods described herein. The present disclosure may be realized in hardware that includes a portion of an integrated circuit that also performs other functions. It may be understood that, depending on the embodiment, some of the steps described above may be eliminated, while other additional steps may be added, and the sequence of steps may be changed.

The present disclosure may also be embedded in a computer program product, which includes all the features that enable the implementation of the methods described herein, and which when loaded in a computer system is able to carry out these methods. Computer program, in the present context, means any expression, in any language, code or notation, of a set of instructions intended to cause a system with an information processing capability to perform a particular function either directly, or after either or both of the following: a) conversion to another language, code or notation; b) reproduction in a different material form. While the present disclosure has been described with reference to certain embodiments, it will be understood by those skilled in the art that various changes may be made, and equivalents may be substituted without departing from the scope of the present disclosure. In addition, many modifications may be made to adapt a particular situation or material to the teachings of the present disclosure without departing from its scope. Therefore, it is intended that the present disclosure is not limited to the particular embodiment disclosed, but that the present disclosure will include all embodiments that fall within the scope of the appended claims.

What is claimed is:

1. An electronic device, comprising:
circuitry configured to:
    receive robot capability parameters associated with a human-machine interaction (HMI) device;
    receive touch parameters associated with a physical-interaction of the HMI device and a user;
    receive control parameters associated with an operator of the HMI device to control the physical-interaction of the HMI device;
    control the physical interaction of the HMI device based on the received robot capability parameters, the received touch parameters, and the received control parameters;
    determine a physical response of the user, based on the control of the physical interaction of the HMI device;
    determine safety metrics associated with the user, based on the determined physical response, the received robot capability parameters, and the received touch parameters;

determine control metrics associated with the operator, based on the received robot capability parameters, and the received control parameters; and control the physical interaction of the HMI device, further based on the determined safety metrics and the determined control metrics, wherein the circuitry is further configured to execute a co-design evaluation procedure comprising at least two iterations, wherein each iteration includes:

(i) receiving one or more subjective metrics indicating a perceived safety or perceived comfort of the user with respect to the physical interaction;

(ii) receiving one or more objective metrics indicative of the physical response of the user captured by one or more sensors during the physical interaction; and (iii) updating at least one of the touch parameters or the control parameters for a subsequent iteration based on the subjective metrics and the objective metrics.

2. The electronic device according to claim 1, wherein the robot capability parameters associated with the HMI device includes at least one of: a form factor parameter of the HMI device, a level of autonomy of the HMI device, or a degree of freedom of the HMI device.

3. The electronic device according to claim 1, wherein the touch parameters include at least one of: an orientation of the HMI device, a speed of a part of the HMI device, a force applied by the HMI device, a time duration for an operation of the HMI device, or a contact zone between the HMI device and the user.

4. The electronic device according to claim 1, wherein the control parameters associated with the operator include at least one of: operator-control freedom parameters associated with the HMI device, a touch-based feedback from the patient, or a user interface control associated with the operator.

5. The electronic device according to claim 1, wherein the determined safety metrics associated with the user includes at least one of: a trust level of the user associated with the HMI device, a comfort level of the user associated with the HMI device, or a safety level of the user associated with the HMI device.

6. The electronic device according to claim 1, wherein the physical response of the user includes at least one of: a body movement of the user, a gaze of the user, a verbal response of the user, or a facial response of the user.

7. The electronic device according to claim 1, wherein the control metrics include at least one of: a physical load on the operator, a mental load on the operator, a level of control of operator, a level of awareness of the operator, or a task performance by the HMI device.

8. The electronic device according to claim 1, wherein the circuitry is further configured to: receive user-background parameters associated with the user, wherein the received user-background parameters include at least one of: a physical condition of the user, an age of the user, a gender of the user, or an ethnicity of the user.

9. The electronic device according to claim 8, wherein the received user-background parameters are correlated with a trust level of the user associated with the HMI device.

10. The electronic device according to claim 1, wherein the circuitry is further configured to: receive operator-background parameters associated with the operator, wherein the received operator-background parameters include at least one of: an identity of the operator, a type of operation of the operator, a gender of the operator, and a relationship between a patient and the operator.

11. The electronic device according to claim 10, wherein the received operator-background parameters are correlated with a trust level of the user associated with the HMI device.

12. The electronic device according to claim 1, wherein the circuitry is further configured to: determine first communication metrics associated with the user and the HMI device; and determine second communication metrics associated with the user and the operator, wherein a trust level of the user of the HMI device is correlated with the determined first communication metrics and the determined second communication metrics.

13. A method, comprising:

in an electronic device:

receiving robot capability parameters associated with a human-machine interaction (HMI) device;

receiving touch parameters associated with a physical interaction of the HMI device and a user;

receiving control parameters associated with an operator of the HMI device to control the physical interaction of the HMI device;

controlling the physical interaction of the HMI device based on the received robot capability parameters, the received touch parameters, and the received control parameters;

determining a physical response of the user, based on the control of the physical interaction of the HMI device;

determining safety metrics associated with the user, based on the determined physical response, the received robot capability parameters, and the received touch parameters;

determining control metrics associated with the operator, based on the received robot capability parameters, and the received control parameters; and controlling the physical interaction of the HMI device, further based on the determined safety metrics and the determined control metrics; and executing a co-design evaluation procedure comprising at least two iterations, wherein each iteration includes: receiving one or more subjective metrics indicating a perceived safety or perceived comfort of the user with respect to the physical interaction; receiving one or more objective metrics indicative of the physical response of the user captured by one or more sensors during the physical interaction; and updating at least one of the touch parameters or the control parameters for a subsequent iteration based on the subjective metrics and the objective metrics.

14. The method according to claim 13, wherein the robot capability parameters associated with the HMI device includes at least one of: a form factor parameter of the HMI device, a level of autonomy of the HMI device, or a degree of freedom of the HMI device.

15. The method according to claim 13, wherein the touch parameters include at least one of: an orientation of the HMI device, a speed of a part of the HMI device, a force applied by the HMI device, a time duration for an operation of the HMI device, or a contact zone between the HMI device and the user.

16. The method according to claim 13, wherein the control parameters associated with the operator include at least one of: operator-control freedom parameters associated with the HMI device, a touch-based feedback from the patient, or a user interface control associated with the operator.

17. The method according to claim 13, wherein the determined safety metrics associated with the user includes at least one of: a trust level of the user associated with the HMI device, a comfort level of the user associated with the HMI device, or a safety level of the user associated with the HMI device.

18. The method according to claim 13, wherein the physical response of the user includes at least one of: a body movement of the user, a gaze of the user, a verbal response of the user, or a facial response of the user.

19. The method according to claim 13, wherein the control metrics include at least one of: a physical load on the operator, a mental load on the operator, a level of control of operator, a level of awareness of the operator, or a task performance by the HMI device.

20. A non-transitory computer-readable medium having stored thereon, computer-executable instructions that when executed by an electronic device, causes the electronic device to execute operations, the operations comprising:

receiving robot capability parameters associated with a human-machine interaction (HMI) device;

receiving touch parameters associated with a physical interaction of the HMI device and a user;

receiving control parameters associated with an operator of the HMI device to control the physical interaction of the HMI device;

controlling the physical interaction of the HMI device based on the received robot capability parameters, the received touch parameters, and the received control parameters;

determining a physical response of the user, based on the control of the physical interaction of the HMI device;

determining safety metrics associated with the user, based on the determined physical response, the received robot capability parameters, and the received touch parameters;

determining control metrics associated with the operator, based on the received robot capability parameters, and the received control parameters; and controlling the physical interaction of the HMI device, further based on the determined safety metrics and the determined control metrics, wherein the operations further comprise executing a co-design evaluation procedure comprising at least two iterations, wherein each iteration includes: receiving one or more subjective metrics indicating a perceived safety or perceived comfort of the user with respect to the physical interaction; receiving one or more objective metrics indicative of the physical response of the user captured by one or more sensors during the physical interaction; and updating at least one of the touch parameters or the control parameters for a subsequent iteration based on the subjective metrics and the objective metrics.

\* \* \* \* \*